(12) United States Patent
Van Vreeland et al.

(10) Patent No.: US 8,276,623 B2
(45) Date of Patent: Oct. 2, 2012

(54) DEVICE FOR AUTOMATICALLY FILLING PRODUCT CONTAINERS WITH A LIQUID COMPRISING ONE OR MORE MEDICINES

(75) Inventors: Sander Godfried Van Vreeland, Enschede (NL); Jan Willem Dorpema, Veenendaal (NL)

(73) Assignee: Medical Dispensing Systems B.V., Enschede (NL)

( * ) Notice: Subject to any disclaimer, the term of this patent is extended or adjusted under 35 U.S.C. 154(b) by 963 days.

(21) Appl. No.: 11/911,560

(22) PCT Filed: Apr. 13, 2006

(86) PCT No.: PCT/NL2006/000197
§ 371 (c)(1),
(2), (4) Date: Oct. 17, 2008

(87) PCT Pub. No.: WO2006/110036
PCT Pub. Date: Oct. 19, 2006

(65) Prior Publication Data
US 2009/0038709 A1 Feb. 12, 2009

(30) Foreign Application Priority Data
Apr. 13, 2005 (NL) .................................. 1028756

(51) Int. Cl.
*B65B 1/04* (2006.01)

(52) U.S. Cl. .......... 141/27; 141/104; 141/266; 141/270; 141/284; 141/330

(58) Field of Classification Search .................. 141/21, 141/25, 27, 100, 102–104, 114, 250, 251, 141/266, 267, 269, 270, 275, 284, 329, 330
See application file for complete search history.

(56) References Cited

U.S. PATENT DOCUMENTS

| | | | |
|---|---|---|---|
| 5,056,568 A | 10/1991 | DiGianfilippo et al. | |
| 5,431,201 A * | 7/1995 | Torchia et al. | 141/98 |
| 7,017,623 B2 * | 3/2006 | Tribble et al. | 141/27 |

* cited by examiner

*Primary Examiner* — Gregory Huson
*Assistant Examiner* — Jason K Niesz
(74) *Attorney, Agent, or Firm* — Robert A. Jensen; Jensen & Puntigam, P.S.

(57) ABSTRACT

The invention relates to a device for filling one or more product containers with a liquid comprising one or more medicines. The device comprises a housing at least provided in a position of use with an array of medicine containers, at least some of which are provided with concentrated liquid components of the one or more medicines. The housing is also provided with an automatic machine which is adapted to manipulate a syringe for measured take-up of liquid from a medicine container. The automatic machine is adapted to rotate the medicine container transversely of its longitudinal axis.

14 Claims, 8 Drawing Sheets

DEVICE FOR AUTOMATICALLY FILLING PRODUCT CONTAINERS WITH A LIQUID COMPRISING ONE OR MORE MEDICINES

TECHNICAL FIELD

The invention relates to a device for filling one or more product containers with a liquid comprising one or more medicines, comprising a housing at least provided in a position of use with an array of second or medicine containers, at least some of which are provided with concentrated liquid components of the one or more medicines, which housing is provided with a automatic machine which is adapted to manipulate a syringe for measured take-up of liquid from a medicine container.

BACKGROUND OF THE INVENTION

The liquid with medicines to be added to a product container, such as an infusion bag, is in practice usually prepared manually by drawing a precisely determined quantity of dissolving liquid and/or diluent liquid out of a first container using a syringe, adding this dissolving liquid and/or diluent liquid to a second container having therein a solid component of a medicine, subsequently shaking this second container until the solid component is dissolved, and then adding a precisely determined quantity to the infusion bag. Because more than one component must sometimes be added, this method sometimes has to be repeated several times. With the thus filled second containers multiple infusion bags can then generally be prepared in accordance with a predetermined prescription.

The known method has a number of drawbacks. In the first place it is not possible to preclude the health of people carrying out the method day after day from being damaged, because many medicines, including cytostatics, radiopharmaceuticals, antibiotics and antibodies, can be to a greater or lesser extent harmful to health. Nor is it possible to preclude people carrying out the method day after day from developing RSI-type complaints because the same operations must be continually repeated. There is further also a risk for the patient, because mistakes cannot be precluded. Because infusion bags containing medicines must generally be unavailable within several hours, preparation practically always takes place in the hospital in which the patient is being nursed or treated. The number of preparations is continuously increasing, which has the result in many cases that the cleanroom of the hospital in which the method is applied is almost everywhere too small. A conversion in which the cleanroom is extended is very disruptive to operations and moreover expensive, while adding a second cleanroom a distance away is not attractive from a logistics viewpoint.

A device according to the preamble is known in practice with which the above described method can be performed in at least partially automated manner so as to thus avoid the associated problems.

The known device is suitable for automatically filling a product container in the form of a syringe with a liquid comprising one or more medicines. The known device comprises for this purpose an automatic machine which is adapted to manipulate the syringe for measured take-up of a diluent liquid from a first container and for subsequent addition thereto of a concentrated liquid component of a medicine by measured take-up thereof from a second container.

In the known device the containers hang upside down in the housing in order to facilitate take-up of liquid from the containers. This inevitably results in the containers beginning to leak. Not only are costly liquids lost here, but this also entails a health hazard for the people operating the device.

DISCLOSURE OF THE INVENTION

The invention has for its object to provide an improved device of the type stated in the preamble which obviates these drawbacks.

The device according to the invention has for this purpose the feature that the automatic machine is adapted to rotate the medicine container substantially transversely of its longitudinal axis.

In the device according to the invention the medicine containers stand upright in the housing and these are placed upside down one by one if fluid has to be removed from a relevant medicine container. The chance of leakage is hereby reduced to a minimum.

In a more extensive preferred embodiment the automatic machine is also provided in a position of use with an array of first or additional containers with diluent liquids, and the automatic machine is further adapted to manipulate the syringe for measured take-up of liquid out of or measured delivery of liquid to, as well as transport of liquid between, an additional container and a medicine container, wherein the automatic machine is adapted to rotate both the additional container and the medicine container substantially transversely on their longitudinal axis. In this preferred embodiment the device according to the invention is also suitable for diluting the concentrated medicinal liquid from the medicine container.

In an even more extensive preferred embodiment at least some of the array of medicine containers are provided with solid components of the one or more medicines, and at least some of the array of additional containers are provided with dissolving liquids. In this even more extensive preferred embodiment the device according to the invention is also suitable for dissolving solid components of a medicine from the medicine container.

In a first preferred embodiment the automatic machine is adapted to rotate the syringe substantially transversely of its longitudinal axis substantially simultaneously with the medicine container or the additional container. In one simultaneous movement the automatic machine brings the syringe together with the container for manipulating into the proper starting position. This movement can be performed using only one compact automatic machine.

According to a universal preferred embodiment, the automatic machine is provided with a syringe holder with clamping means and with a preferably remotely controllable drive for moving the clamping means toward each other in order to clamp a syringe. The device is now suitable for manipulating syringes of different thickness.

The universal character of the device according to the invention is further developed in an embodiment in which the syringe holder is provided with means for engaging on the plunger of the syringe, wherein the mutual distance between the means is adjustable, preferably by means of a remote-control. The device is now suitable for manipulating syringes with different dimensions of the plunger.

According to a further development of the universal embodiment, the automatic machine is provided with gripping means with a mutual distance preferably adjustable by means of a remote-control for the purpose of a gripping an additional container or a medicine container. The device is now suitable for manipulating containers of different dimensions.

The distance between the syringe holder and the gripping means is preferably adjustable, for instance by means of a remote-control, so that the device is suitable for manipulating syringes of differing lengths.

In a particularly accurate embodiment, means are accommodated in the housing for weighing the additional container and/or the medicine container prior to take-up of liquid from and delivery of liquid to the relevant container by a syringe. The amount of liquid taken up from or delivered to a container can thus be monitored fully automatically.

A further development of the invention has the feature that the automatic machine is adapted to shake the additional and/or the second container, whereby the mixing process is enhanced and a usable dilution or solution can be obtained more rapidly, and it is moreover possible to work at all times with a homogenous dilution or solution.

According to another embodiment, the automatic machine is adapted to rotate the syringe around its longitudinal axis, so that syringes which have to be screwed on can also be utilized.

An extremely safe realization of the device according to the invention has the feature that the additional containers and/or the medicine containers and/or the product containers are provided with identification labels, and that the automatic machine is provided with a read device for reading an identification label of a container, and with means for comparing the data of the identification label with a list of data made available beforehand prior to take-up of liquid from and delivery of liquid to the container by a syringe. All process steps can hereby be verified during preparation. The automatic machine is preferably also provided here with a write device for writing an identification label of a product container filled with a liquid comprising one or more medicines. The content of the various containers can hereby also be checked after preparation, and a filled product container can be identified so as to preclude possible confusion. The automatic machine is preferably also provided with an input means for inputting a list of components for a product container.

BRIEF DESCRIPTION OF THE DRAWINGS

The invention will now be further elucidated with reference to the following figures, in which.

BEST MODE FOR CARRYING OUT THE INVENTION

Figure 1:
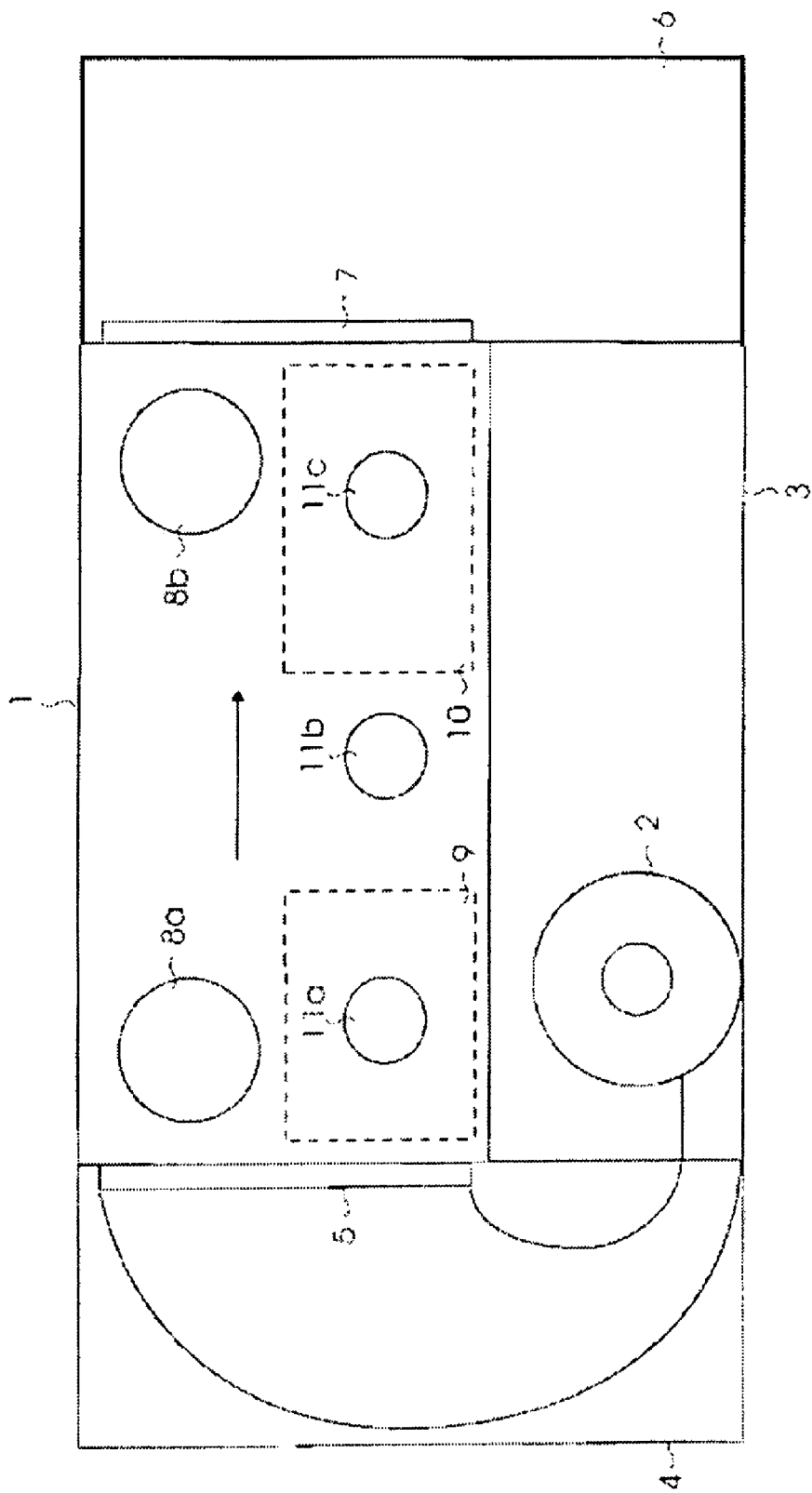
FIG. 1 shows in schematic side view a device according to the invention.

FIG. 1 shows in schematic side view a device according to the invention consisting of a ventilated housing container or housing 1 in which the actual filling of infusion bags takes place and in which an airflow indicated with an arrow is maintained using a fan 2 placed in a bottom cabinet 3. The air is blown into ventilated housing 1 via a supply cabinet 4 with an inlet filter 5 place therein, whereby an aseptic environment can be maintained in ventilated housing 1. Air from ventilated housing 1 is relinquished to the outside air via a discharge cabinet 6 and an outlet filter 7 placed therein, wherein outlet filter 7 ensures that no toxic substances enter the atmosphere. Ventilated housing 1 is provided with sluices 8a,8b known in the field and via which sterile syringes, infusion bags filled with physiological salt solution and/or glucose and the like can be placed in a feed magazine 9, and via which infusion bags, to which one or more medicines are added according to prescription, can be removed from a discharge magazine 10, wherein use can be made of glove boxes 11a, 11b, 11c known in the field.

Figure 2:
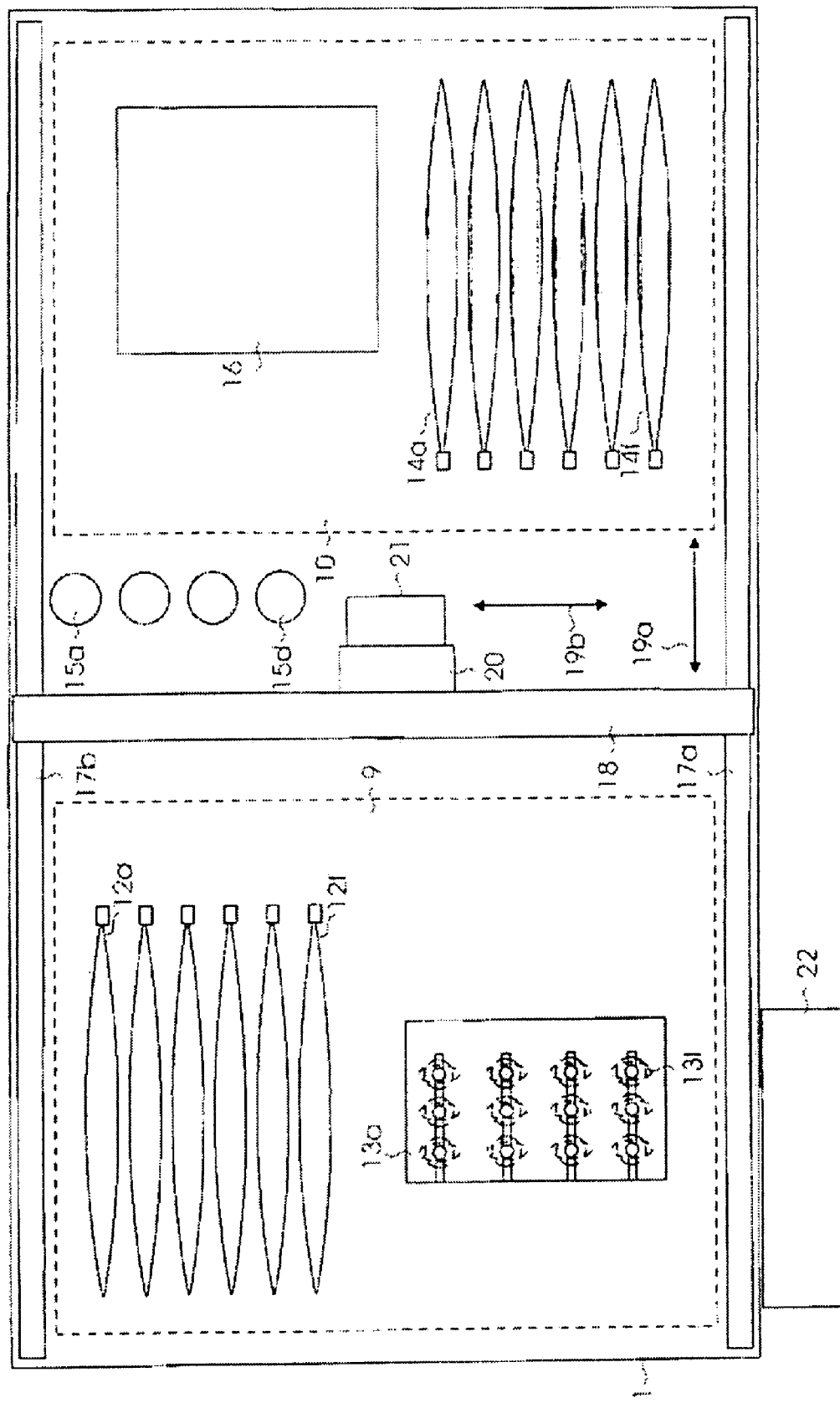
FIG. 2 shows in schematic top view a ventilated housing according to the invention.

FIG. 2 shows a schematic top view of a ventilated housing 1 according to the invention. Ventilated housing 1 comprises a feed magazine 9 in which infusion bags 12a, . . . , 12f placed in racks and filled with physiological salt solution and/or glucose and the like are placed and in which a rack with empty clean syringes 13a, . . . , 13l is also placed. Ventilated housing 1 further comprises a discharge magazine 10 in which infusion bags 14a, . . . , 14f placed in racks and filled with physiological salt solution and/or glucose and the like are placed to which one or more medicines have been or are added according to prescription. In addition, there is also a rack in which bottles 15a, . . . , 15d with powdered or highly concentrated cytostatics are stored and a waste container 16 in which used syringes can be discarded. Two rails 17a,17b are mounted in ventilated housing 1 close to the front and rear wall, on which rails a transverse rail 18 can move in the direction of arrow 19a using a drive (not shown), and a carriage 20 is mounted on transverse rail 18 which can move in the direction of arrow 19b using a drive (not further shown), this in a manner self-evident to a skilled person such that carriage 20 can be placed above almost any position in ventilated housing 1. Mounted on carriage 20 is a schematically represented syringe manipulator 21, using which the inventive method is performed. For control of carriage 20 and of syringe manipulator 21 the ventilated housing 1 is provided with an input means 22 with which commands can be given manually and with which prescriptions can be read from a suitable data carrier.

Figure 3:
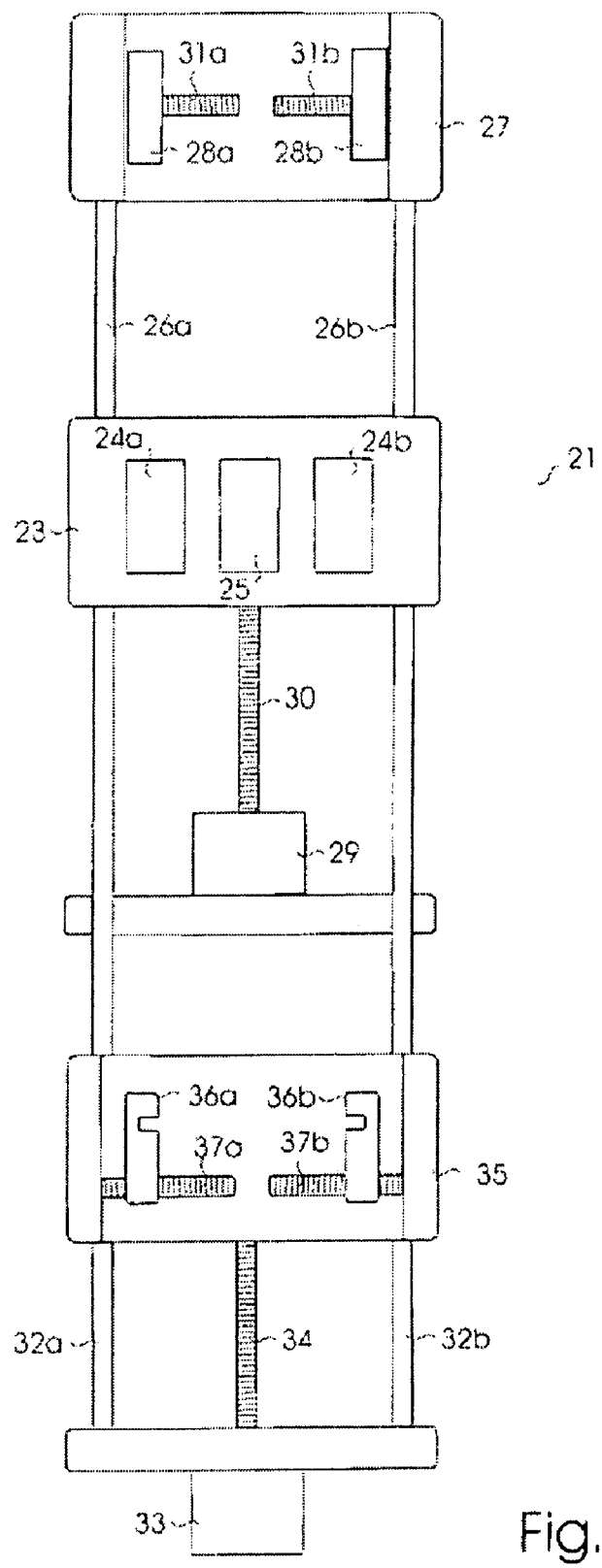
FIG. 3 shows a schematic front view of a possible embodiment of a syringe manipulator.

FIG. 3 shows a schematic front view of a possible embodiment of a syringe manipulator 21. Syringe manipulator 21 consists of a syringe holder 23 which is mounted on carriage 20 for rotation around a shaft situated perpendicularly of the plane of the figure and which is provided with two rollers 24a,24b which can move toward each other using a drive (not shown) such that a syringe placed therebetween is clamped. The syringe then rests here against a third roller 25 which can rotate using a drive (not shown), whereby the syringe will begin to rotate around a longitudinal axis. Mounted slidably on syringe holder 23 are two shafts 26a,26b to which is attached a gripper 27 provided with two fingers 28a,28b with which for instance a bottle 15 can be grasped. The distance between syringe holder 23 and gripper 27 can be set using a drive 29 and a screw spindle 30, while the distance between fingers 28a,28b can be set using a drive (not shown) and screw spindles 31a,31b. Further attached fixedly to syringe holder 23 are two shafts 32a,32b on which an injector 35 is mounted slidably using a drive, 33 and a screw spindle 34, with which injector a plunger of a syringe can be grasped with two fingers 36a,36b and screw spindles 37a,37b.

The above stated drives for setting the distance between different components are preferably adapted such that they are remotely controllable. The automatic machine can hereby be changed over fully automatically.

Figure 4:
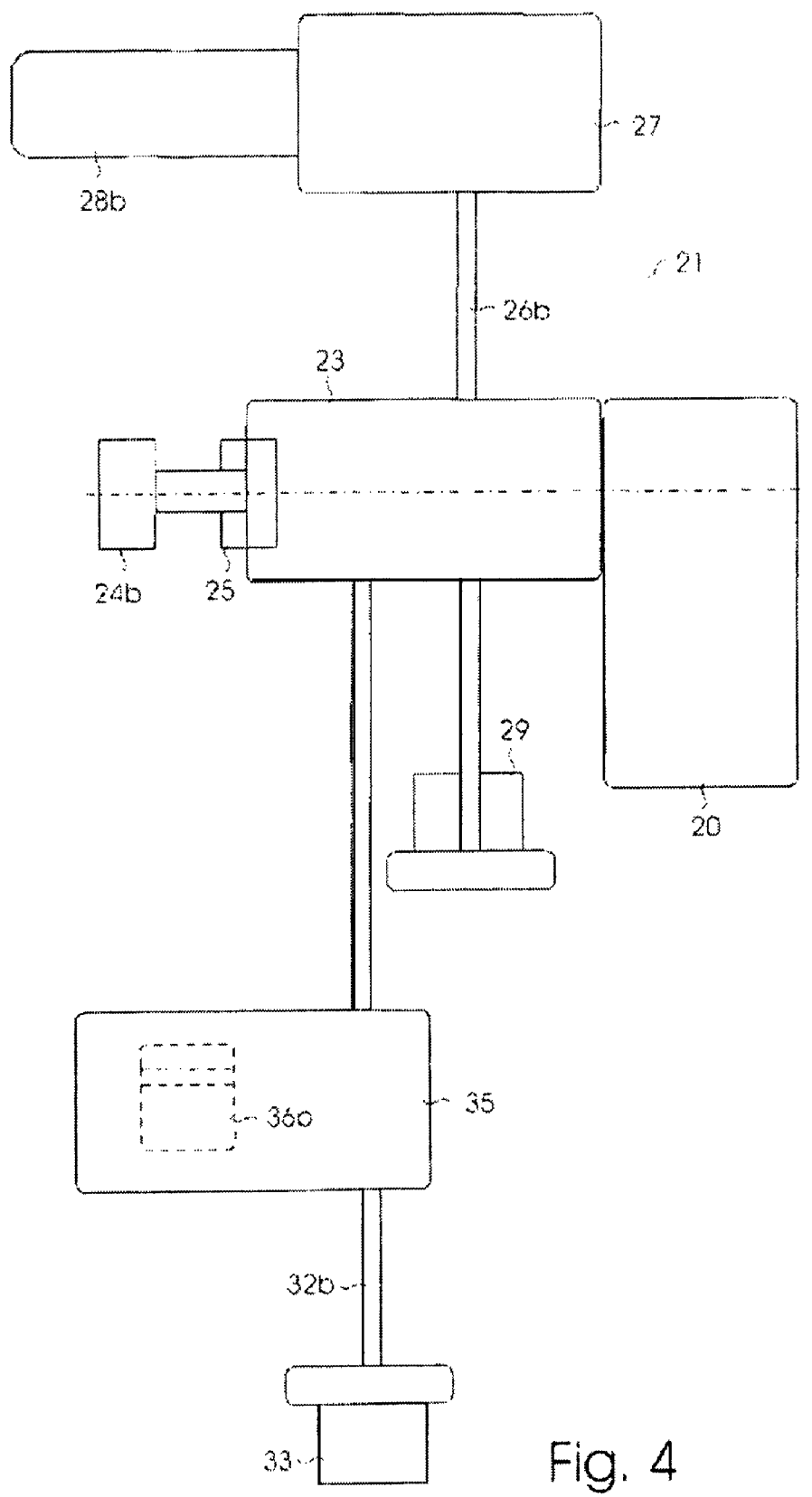
FIG. 4 shows a schematic side view of this syringe manipulator.

FIG. 4 shows a schematic side view of this syringe manipulator 21, with syringe holder 23 mounted rotatably on carriage 20, with rollers 24b and rotatable third roller 25, with shaft 26b and gripper 27 with finger 28b with which for instance a bottle 15 can be grasped. Further shown are shaft 32b, drive 33 and injector 35, with which a plunger of a syringe can be grasped, and finger 36b.

Figure 5:
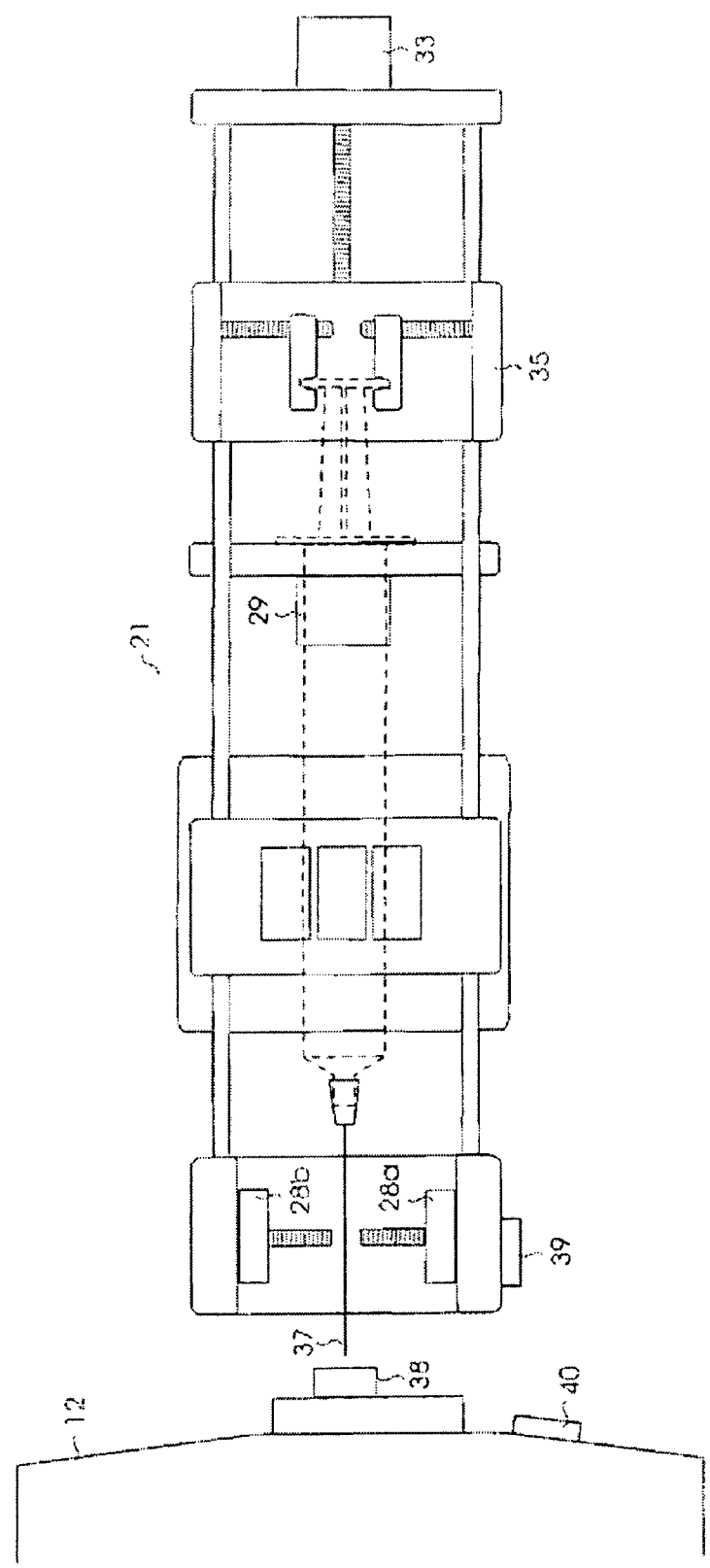
FIG. 5 shows a schematic side view of the filling of a syringe.

FIG. 5 shows a schematic side view of the filling of a syringe, wherein a needle 37 pierces septum 38 of an infusion bag 12, whereafter the desired amount of liquid is drawn into the syringe using drive 33 and injector 35. If desired, a chip 40 on infusion bag 12 can be read beforehand using a read/write device 39 known in the field in order to reduce the chance of errors, and the read value can be written into chip 40. Instead of infusion bags provided with a septum, use can also be made of infusion bags with a screw system. In that case syringes with a screw system must also be used, wherein fingers 28a, 28b can advantageously be utilized to unscrew the protective cap from the syringe beforehand.

Figure 6:
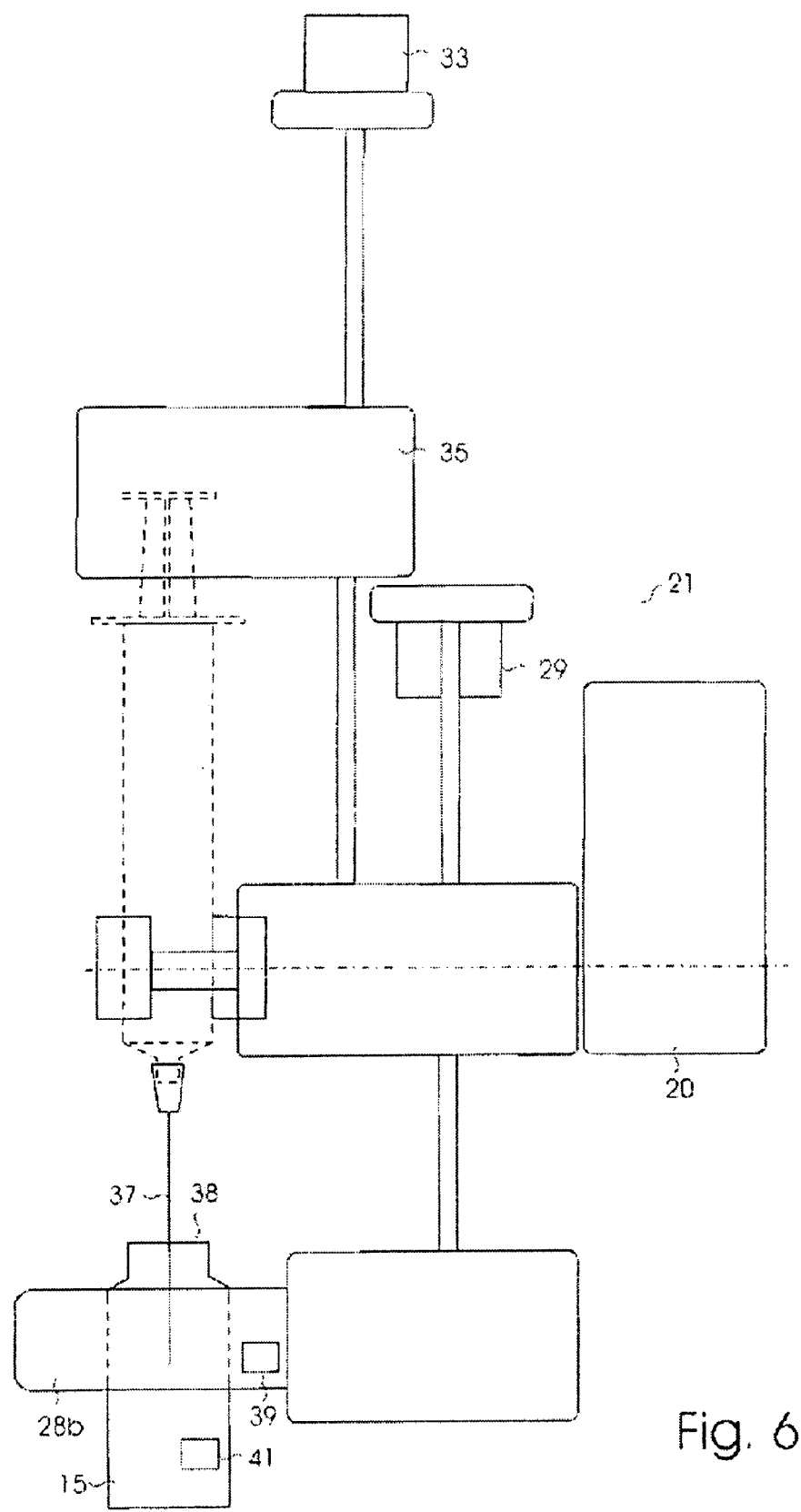
FIG. 6 shows a schematic side view of the filling of a bottle.

FIG. 6 shows a schematic side view of the filling of a bottle 15, wherein needle 37 pierces septum 38 of a bottle 15, whereafter the desired amount of liquid can be injected into the bottle using drive 33 and injector 35. If desired, a chip 41 on bottle 15 can be read beforehand using read/write device 39 in order to reduce the chance of errors, and the injected quantity can be written into chip 41. After filling the needle 37 is withdrawn from bottle 15 and the bottle is shaken by moving carriage 20 rapidly back and forth along transverse rail 18.

Figure 7:
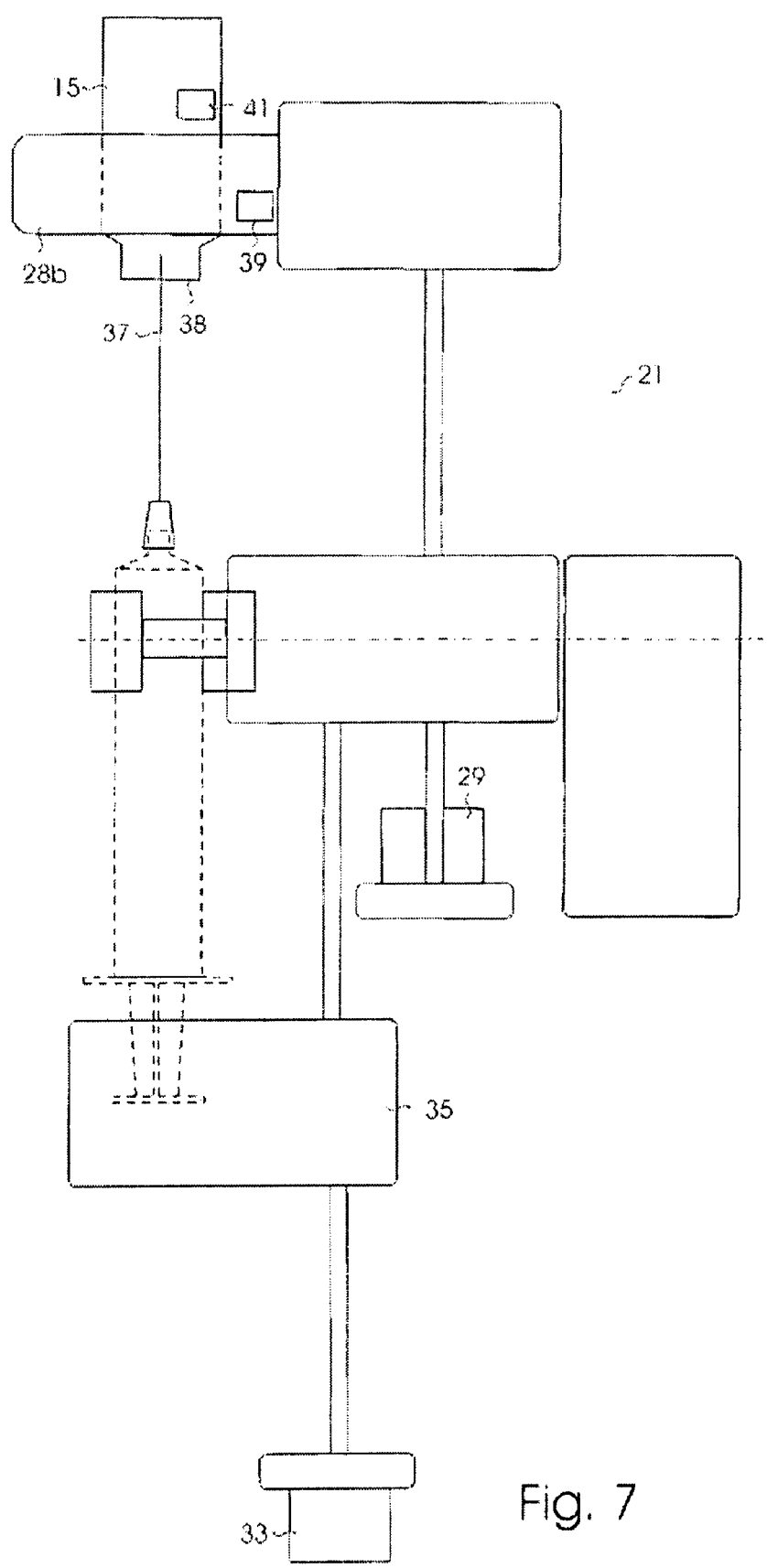
FIG. 7 shows a schematic side view of the removal of liquid from a bottle.

FIG. 7 shows a schematic side view of the removal of liquid from bottle 15, wherein bottle 15 is turned over so that the last remnant of the often costly liquid in bottle 15 can also be utilized.

Figure 8:
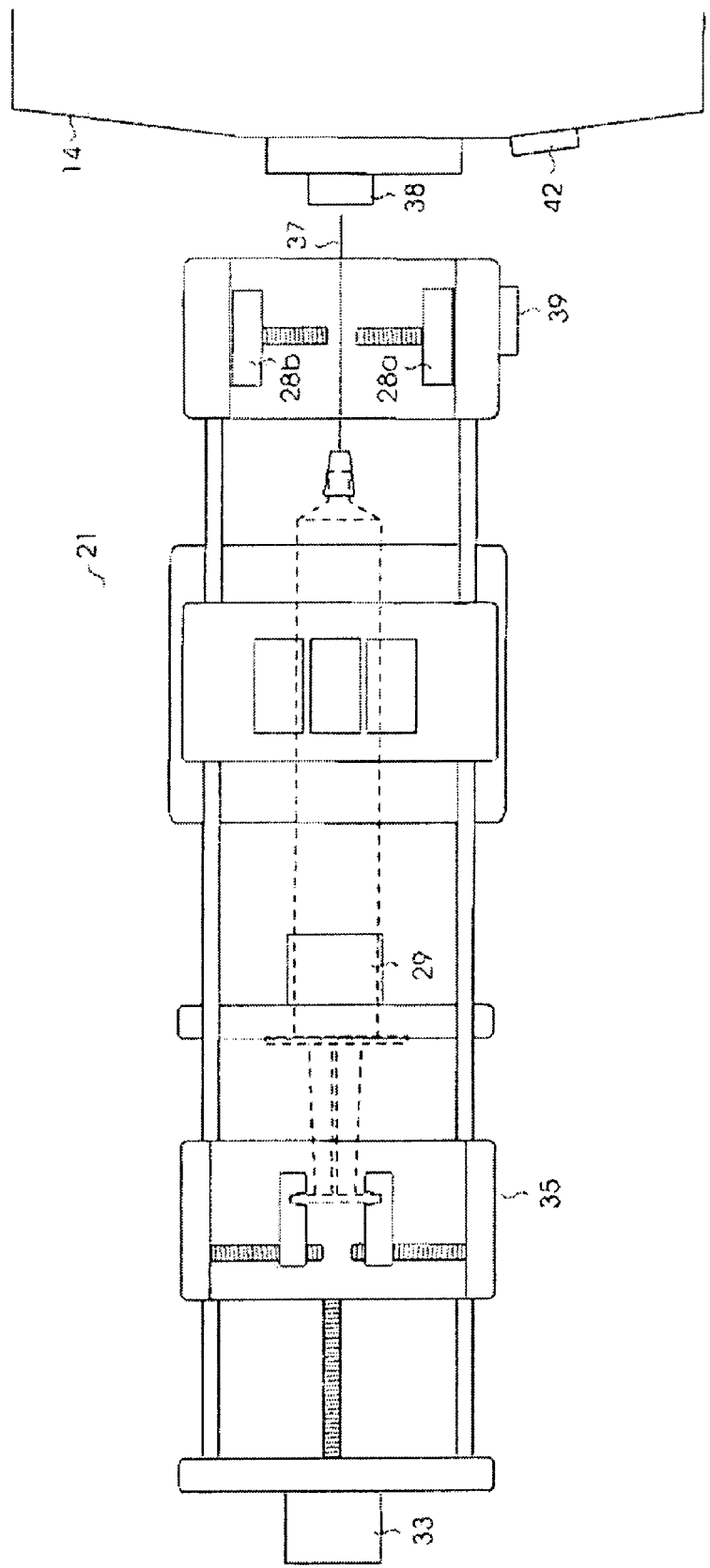
FIG. 8 shows schematically the injecting of liquid into an infusion bag.

FIG. 8 shows schematically the injection of liquid into an infusion bag, wherein a needle 37 pierces septum 38 of an infusion bag 14, whereafter the desired amount of liquid is injected into infusion bag 14 using drive 33 and injector 35. If desired, a chip 42 on infusion bag 14 can be read beforehand using a read/write device 39 known in the field in order to reduce the chance of errors, and the read value can be written into chip 42.

A weighing element can optionally be incorporated in the housing in order to weigh a container before and after manipulation by a syringe. This enables an automatic check on the dosage. The weighing element is preferably placed in the vicinity of the medicine containers and/or additional containers to be manipulated. In the shown preferred embodiment the weighing element can be placed adjacently of the rack with bottles 15 (see FIG. 2). Weighing elements suitable for this purpose are commercially available per se.

It is noted that although the housing is preferably ventilated and provided with an internally aseptic inner side, it can nevertheless always be placed outside the clean room. The syringes, first containers and second containers required in the housing must however preferably be placed in per se known holders in the clean room, and be introduced into the housing for instance a known sluice system, while the filled product containers can be removed in similar manner. However, the handling of closed additional containers, medicine containers and filled product containers involves practically no risks.

It is noted for the sake of completeness that although the figures illustrate filling of a product container in the form of an infusion bag, it will undoubtedly be immediately apparent to a skilled person that the invention is not limited thereto. An example of another type of product container suitable for filling with a liquid with medicines is a syringe.

The device according to the invention is generally suitable for preparing diverse medicines in liquid form and herein provides many advantages as described above. The device according to the invention is particularly suitable for preparing liquid medicines which are harmful to health, such as medicines comprising cytotoxic substances.

The invention claimed is:

1. Device for filling one or more product containers with a liquid comprising one or more medicines, comprising a housing at least provided in a position of use with an array of medicine containers, at least some of which are provided with concentrated liquid components of the one or more medicines, which housing is provided with an automatic machine which is adapted to manipulate a syringe for measured take-up of liquid from a medicine container, characterized in that the automatic machine is adapted to rotate the medicine container substantially transversely of its longitudinal axis, and wherein the automatic machine is adapted to rotate the syringe substantially transversely of its longitudinal axis substantially simultaneously with the medicine container, wherein the automatic machine is provided with a syringe holder with clamping means and with a preferably remotely controllable drive for moving the clamping means toward each other in order to clamp a syringe, wherein the automatic machine is provided with gripping means with a mutual distance preferably adjustable by means of a remote-control for the purpose of gripping a medicine container, wherein the gripping means are mounted slidably on the syringe holder.

2. Device as claimed in claim 1, wherein the housing is also provided in a position of use with an array of additional containers with diluent liquids, and wherein the automatic machine is further adapted to manipulate the syringe for measured take-up of liquid out of or measured delivery of liquid to, as well as transport of liquid between, an additional container and a medicine container, wherein the automatic machine is adapted to rotate both the additional container and the medicine container substantially transversely on their longitudinal axis and wherein the automatic machine is adapted to rotate the syringe substantially transversely of its longitudinal axis substantially simultaneously with the medicine container or the additional container.

3. Device as claimed in claim 2, wherein at least some of the array of medicine containers are provided with solid components of the one or more medicines, and at least some of the array of additional containers are provided with dissolving liquids.

4. Device as claimed in claim 1, wherein the syringe holder is provided with means for engaging on the plunger of the syringe, wherein the mutual distance between the means is adjustable, preferably by means of a remote-control.

5. Device as claimed in claim 1, wherein the distance between the syringe holder and the gripping clamping means is adjustable, for instance by means of a remote-control.

6. Device as claimed in claim 1, wherein means are accommodated in the housing for weighing the additional and/or the medicine container prior to take-up of liquid from and delivery of liquid to the container by a syringe.

7. Device as claimed in claim 2, wherein the automatic machine is adapted to shake the additional container and/or the medicine container.

8. Device as claimed in claim 2, wherein medicine containers and/or additional containers and/or product containers are provided with identification labels, and wherein the automatic machine is provided with a read device for reading an identification label of a container, and with means for comparing the data of the identification label with a list of data made available beforehand prior to take-up of liquid from and delivery of liquid to the container by a syringe.

9. Device as claimed in claim 5, wherein the automatic machine is provided with a write device for writing an identification label of a product container filled with a liquid comprising one or more medicines.

10. Device as claimed in claim 5, wherein the housing is provided with an input means for inputting a list of components for a product container.

11. Device as claimed in claim 1, wherein the product containers are infusion bags or syringes.

12. Device as claimed in claim 1, wherein one or more of the medicines comprises cytotoxic substances.

13. Device as claimed in claim 1, wherein the housing is ventilated.

14. Device as claimed in claim 1, wherein in a position of use the housing is provided with an array of product containers at least partially filled with a liquid.

\* \* \* \* \*